United States Patent [19]

Sun

[11] Patent Number: 5,925,586
[45] Date of Patent: Jul. 20, 1999

[54] PHOSPHORUS MODIFIED SMALL PORE MOLECULAR SIEVE CATALYSTS, AND THEIR USE IN THE PRODUCTION OF LIGHT OLEFINS

[75] Inventor: Hsiang-ning Sun, Houston, Tex.

[73] Assignee: Exxon Chemical Patents, Inc., Houston, Tex.

[21] Appl. No.: 08/943,984

[22] Filed: Oct. 3, 1997

Related U.S. Application Data

[60] Provisional application No. 60/033,953, Dec. 31, 1996.

[51] Int. Cl.$^6$ ............................. B01J 29/06; B01J 27/16
[52] U.S. Cl. ............................. 502/62; 502/60; 502/64; 502/85; 502/162; 502/208
[58] Field of Search ............................. 502/60, 62, 64, 502/85, 162, 208

[56] References Cited

U.S. PATENT DOCUMENTS

| | | | |
|---|---|---|---|
| 3,911,041 | 10/1975 | Kaeding et al. | 260/682 |
| 4,049,573 | 9/1977 | Kaeding . | |
| 4,409,132 | 10/1983 | Forbus et al. | 502/62 |
| 4,752,596 | 6/1988 | Bergna et al. | 502/64 |
| 5,110,776 | 5/1992 | Chitnis et al. | 502/64 |
| 5,126,298 | 6/1992 | Absil et al. . | |

FOREIGN PATENT DOCUMENTS 2 285 176   4/1976   France .

OTHER PUBLICATIONS

PCT/US97/23736 International Search Report (Jun. 1998).

*Primary Examiner*—Thomas Dunn
*Attorney, Agent, or Firm*—Bradley A. Keller

[57] ABSTRACT

A process for the modification of a small pore molecular sieve catalyst to increase its selectivity to ethylene in the production of light olefins from oxygenated compounds, particularly methanol. The catalyst is modified with phosphorus by incorporating a phosphonitrilic oligomer with the catalyst, and then calcining the catalyst at temperature sufficient to decompose the phosphonitrilic oligomer, and deposit from about 0.001 wt. % to about 50 wt. % phosphorus on the catalyst. This modification provides a novel composition in that it increases the ethylene selectivity of the catalyst in the production of light olefins from oxygenates as contrasted with a small pore molecular sieve catalyst otherwise similar except that it has not been so treated and modified with the phosphonitrilic oligomer.

9 Claims, No Drawings

PHOSPHORUS MODIFIED SMALL PORE MOLECULAR SIEVE CATALYSTS, AND THEIR USE IN THE PRODUCTION OF LIGHT OLEFINS

This application claims priority to U.S. Provisional Patent Application No. 60/033,953, filed Dec. 31, 1996.

FIELD OF THE INVENTION

This invention relates to a process for the modification of a small pore molecular sieve catalyst to increase its selectivity in producing ethylene and propylene, particularly ethylene, in the production of light olefins from oxygenates, particularly methanol. It also relates to the modified catalysts as novel compositions of matter, and their use in the process for selectively producing ethylene and propylene, particularly ethylene, with lessened by-products production.

BACKGROUND

It is known to selectively convert oxygenates, including particularly methanol, to light olefins, viz. ethylene ($C_2^=$), propylene ($C_3^=$), and butylene ($C_4^=$). Ethylene and propylene are in high demand, and the need for these chemical raw materials, particularly ethylene, continues to grow. In a current process, methanol is reacted at elevated temperature over a fluidized bed of a molecular sieve catalyst, e.g., ZSM-5 zeolite or SAPO-34, to produce a reaction product from which $C_2$–$C_4$ olefins are recovered.

In producing light olefins, the selectivity to ethylene can be increased to some extent by increasing reactor severity; but this has its limitations because as reactor severity is increased total olefin production is decreased. Moreover, the production of paraffins, i.e., methane, ethane, propane, etc., aromatics and other less desirable components will also increase. Attempts have also been made to modify the framework structure of the catalyst to increase light olefin production, especially the $C_2^=/C_3^=$ ratio, while producing as little of the paraffinic and aromatic by-products as possible.

In U.S. Pat. No. 3,911,041, there is disclosed a process for converting methanol to a reaction product containing light olefins by contact of the methanol with a phosphorus modified zeolite. A zeolite of intermediate pore size, such as ZSM-5, is modified by incorporating from about 0.78 wt. % to 4.5 wt. % phosphorus bonded to its structural framework. Typically the dry ZSM-5 zeolite is contacted with a solution of a phosphorus-containing compound, e.g., $PCl_3$, and heated at elevated temperature for a time sufficient to incorporate the phosphorus within the crystalline framework of the zeolite. In conducting a methanol to olefins reaction with a phosphorus modified ZSM-5 catalyst, as demonstrated by the Patentee, selectivities at 325° C. to the $C_2$–$C_3$ olefins are high compared to the selectivities to the $C_2$–$C_3$ paraffins, but butane production was significant. At temperatures above 325° C. selectivities to the $C_2$–$C_4$ olefins were high compared to the selectivities to the $C_2$–$C_4$ paraffins. At temperatures above 500° C. the concentration of ethylene in the product increased, but propylene remained the major component relative to ethylene. At temperatures below 500° C., at conditions which increased the ratio of ethylene:propylene, the production of butenes, butanes, or both butenes and butanes was increased significantly; sufficiently so that the molar ratio of $C_2^=/C_4$<1. Changing the severity of a reaction to change the distribution of olefins and by-products thus has its limitations.

Other modifications of zeolite catalysts have been proposed, or made, but there remains a pressing need for improving the performance of this type of catalyst for selectively producing light olefins, particularly ethylene, from oxygenates, notably alcohols, with low by-products formation.

SUMMARY OF THE INVENTION

This invention, which meets this and other needs, relates to a process for the modification of a small pore molecular sieve catalyst to increase its selectivity to ethylene when used in the production of light olefins from oxygenated compounds which comprises contacting, and incorporating with the catalyst a phosphonitrilic oligomer formed of phosphazo groups having the formula

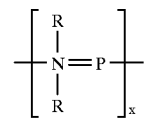

wherein the substituent R is the same or different, and is selected from a group consisting of halogen, alkenyl, alkynyl, alkyl, cycloalkyl, aryl, aralkyl, alkaryl, alkoxy or the like, $\chi$ ranges from about 3 to about 100, the oligomer formed from the phosphazo groups is either linear or cyclic, and calcining the catalyst with which the phosphonitrilic oligomer has been incorporated at temperature sufficient to decompose the phosphonitrilic oligomer, and deposit on the catalyst from about 0.001 percent to about 50 percent phosphorus, based on the total weight of the phosphorus-containing catalyst.

DETAILED DESCRIPTION

This invention, which meets this and other needs, relates to a process for the modification of small pore molecular sieves by contact and treatment with phosphonitrilic oligomers (linear and cyclophosphazene compounds), use of the catalyst in the conversion of oxygenates to olefins, and the catalyst composition which is produced. In conducting the process, molecular sieves of pore size ranging from about 5.0 Angstrom Units, Å, to about 4.0 Å, preferably from about 4.8 Å to about 4.4 Å, are modified by contact, and treatment, with a phosphonitrilic oligomer sufficient to improve its stability and increase its selectivity in producing ethylene in the catalytic conversion of oxygenates, particularly methanol, to light olefins. The phosphonitrilic oligomer is contacted with the molecular sieve, and the molecular sieve modified by such treatment, prior to or at the time of the catalytic conversion of the oxygenate to olefins, i.e., as by pretreatment of a fresh or regenerated catalyst, or by the addition and contact of the phosphonitrilic oligomer with the catalyst during catalyst regeneration, or with the oxygenate feed. In the modification of the catalyst the phosphonitrilic oligomer is decomposed from about 0.001 percent to about 50 percent, preferably from about 0.05 percent to about 40 percent, phosphorus being deposited on the molecular sieve, based on the total weight of the molecular sieve (wt. %; dry basis). The resultant catalyst is stable at high temperature in the presence of steam, and it exhibits good activity maintenance during conversion of oxygenates to olefins, with low by-products formation.

In modifying the small pore molecular sieve in accordance with the practice of this invention, a molecular sieve of pore size less than 5.0 Å, exemplary of which are ZSM-34, SAPO-17, SAPO-18, SAPO-34, erionite or the like, in particulate dry solids form is contacted with a liquid in which the phosphonitrilic oligomer has been dispersed, dissolved, incorporated, or added, in concentration ranging from about 0.001 percent to about 15.0 percent, preferably from about 0.01 percent to about 5.0 percent, based on the total weight of solids (wt. %; dry basis), or the phosphonitrilic oligomer in molten state is heated, or calcined at temperature above about 200° C., preferably above about 300° C., and more preferably within a range of from about 350° C. to about 650° C., for a period sufficient to decompose the phosphonitrilic oligomer and deposit from about 0.001 wt. % to about 50 wt. %, preferably from about 0.05 wt. % to about 40 wt. %, phosphorus on the molecular sieve. Temperature and time are to some extent interrelated, but generally the time period required for adequate calcination ranges from about 0.5 hr. to about 48 hours. The surface between the pores is coated with the phosphorus, inclusive of the surface at the outer perimeters of the pores such that the pore openings are partially restricted in diameter. Partial restriction of the size of the pore diameters permits the free ingress of methanol into the pores, reaction of the methanol within the pores, and a relatively high rate of egress of ethylene from the pores vis-à-vis the rate of egress of propylene, paraffins, aromatics and the like from the pores which are more diffusion limited.

The small pore molecular sieve employed in the reaction is of pore size ranging between about 5.0 Å and 4.0 Å, preferably about 4.8 Å and 4.4 Å, and comprised of a crystalline framework oxide component. It is preferably selected from the group consisting of zeolites, tetrahedral aluminophosphates (ALPOs) and tetrahedral silicoaluminophosphates (SAPOs). More preferably, the crystalline framework oxide component is a tetrahedral silicoaluminophosphate (SAPO), e.g., SAPO-18, SAPO-43 and SAPO44. Generally, the pore apertures of the structure consists of from about 6 to about 10, preferably 8 membered ring structures.

These materials, modified and employed in accordance with this invention, include modified natural and synthetic crystalline structures with tetrahedral framework oxide components such as aluminum, silicon, phosphorus and the like. Exemplary of small pore zeolitic catalysts are ZSM-34, ZK4, ZK-5, zeolite A, zeolite T, chabazite, gmelinite, clinoptilalite, erionite, ZSM-35, rho, offretite and the like; and such non-zeolitic catalysts as ferrierite, levyne, SAPO-17, SAPO-18, SAPO-34, SAPO-43 and SAPO-44.

The small pore molecular sieve, zeolitic and non-zeolitic, is modified by contact and treatment with a phosphonitrilic oligomer, either a linear or cyclic phosphonitrilic oligomer, or phosphazene type compound in which a plurality of phosphazo units, or

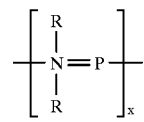

groups, are joined together to form linear chains, or rings of phosphazo units, or groups of alternating phosphorus and nitrogen atoms which form trimers, tetramers, pentamers, hexamers and higher, and the phosphorus atoms are each substituted with a hydrogen reactive substituent R. In the formula the substituents R can be the same or different, and can be halogen, e.g., chlorine, bromine, fluorine, or the like; alkenyl, alkynyl, alkyl, cycloalkyl, or the like, e.g., methyl, ethyl, ethynyl, propyl, butyl or the like; an aryl, e.g., phenyl or the like; an aralkyl or alkaryl, e.g., benzyl, toluyl or the like; alkoxy, e.g., methoxy or the like; or other moiety which will react with hydrogen. In the formula, in forming either a linear or cyclic phosphonitrilic oligomer, $\chi$ can range up to about 100, preferably from about 3 to about 100, and more preferably from about 3 to about 20.

The phosphonitrilic trimer is a preferred oligomer. It is a cyclotriphosphazene type compound, in which three phosphazo groups are joined together to form a six-membered ring, and each of the three phosphorus atoms are substituted with a hydrogen reactive substituent, R. The phosphonitrilic trimer is thus a compound having the formula

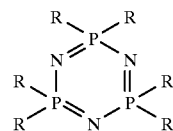

wherein the substituents R can be the same or different, and can be halogen, e.g., chlorine, bromine, fluorine, or the like; alkenyl, alkynyl, alkyl, cycloalkyl, or the like, e.g., methyl, ethyl, ethynyl, propyl, butyl or the like; an aryl, e.g., phenyl or the like; an aralkyl or alkaryl, e.g., benzyl, toluyl or the like; alkoxy, e.g., methoxy or the like; or other moiety which will react with hydrogen. Exemplary of such compounds are hexahalocyclotriphosphazene, hexamethylcyclotriphosphazene, hexaphenylcyclotriphosphazene, or the like. The hexachlorocyclotriphosphazenes have been found to be particularly effective in decomposing and modifying both the zeolites and non-zeolite catalysts by deposition of phosphorus onto the structures.

The phosphonitrilic oligomer, e.g., the trimer, it is believed, is decomposed into substituted phosphazo, di- and tri-phosphazo groups, with one or more of the R substituents thereof reacting with surface attached hydroxyl groups to liberate the hydrogen and form an RH compound, which escapes from the surface, while the phosphorus atom of the mono-, di-, or tri-phosphazo group attaches through the oxygen to the surface of the catalyst; as well as other reactions between the phosphazo groups which link together, bridge over, and cover the surface of the catalyst, inclusive of the areas around the pore openings to restrict the size of the pore exits and reduce the transport rate of exit of molecules larger than ethylene. In other words, due to the restriction of the pore openings the rate of exit of ethylene is increased relative to the rate of exit of the larger $C_3$ molecules, as a consequence of which the modification causes an increase in the formation of ethylene vis-à-vis the $C_3$ and higher in the conversion of methanol to light olefins. The modified catalyst is more stable to high temperature and steam, the yield of ethylene is increased, and the yield of propylene and paraffins are reduced as contrasted with the concentration of these products employing an unmodified but otherwise similar catalyst used at the same conditions for conducting a similar reaction.

The modified catalyst has proven useful in selectively producing ethylene in converting oxygenates, particularly low molecular weight ethers and alcohols, notably dimethyl ether and methanol, to light olefins, with reduced paraffins and by-products formation. An oxygenated feed, e.g., methanol, suitably with added water, is contacted with a fixed, moving, or fluidized bed, or beds, of the modified catalyst at reaction conditions, typically and preferably within the ranges given below:

| Major Operating Variable | Typical Range | Preferred Range |
| --- | --- | --- |
| Temperature, °C. | 250 to 650 | 350 to 500 |
| Pressure, kPa | 0.1 to 200 | 7 to 50 |
| Flow Rate, WHSV (hr$^{-1}$) | 0.01 to 5000 | 0.5 to 2000 | to obtain an effluent from which the ethylene, and other products, is recovered.

The following non-limiting comparative demonstrations and examples illustrate the more salient features of the invention. Temperature is given in Centigrade degrees. All parts, percentages, yields and conversion are given in terms of weight except as otherwise specified.

EXAMPLE 1

Two 5.0 gram portions of SAPO-34 powder from the same batch, obtained from UOP, Des Plaines, Ill., were weighed out, and one was added to a solution of 1.0 gram of phosphonitrilic chloride polymer in 5 cc of dry cyclohexane. The mixture was allowed to stand overnight at room temperature. The solids were then dried at 100° C. for 4 hours, followed by calcination at 650° C.

Both the untreated portion of SAPO-34, referred to in Table 1 as "Unmodified SAPO-34", and the treated portion of SAPO-34, referred to in Table 1 as "Modified SAPO-34", were then employed in similar methanol-to-olefin reactions at similar conditions. Each catalyst was thus evaluated in separate runs at 450° C., 0.7 hr$^{-1}$ WHSV, and 2 psig pressure by contact with a 4:1 mole ratio H O/methanol feed. Reference is made to Table 1.

TABLE 1

| Product Components, Wt. % | Unmodified SAPO-34 | Modified SAPO-34 |
| --- | --- | --- |
| Methane$^{(1)}$ | 3.8 | 3.2 |
| Ethylene | 46.4 | 49.9 |
| Ethane | 1.7 | 1.0 |
| Propylene | 34.3 | 34.6 |

$^{(1)}$Note: Average yield first six hours of run.

The data shows a 3.5 wt. % increase in ethylene production, and a 1 wt. % decrease in (propylene plus methane and ethane) production. In absolute terms there is a small increase in propylene production, with decreased production of paraffins.

Having described the invention, what is claimed is:

1. A process for the modification of a small pore molecular sieve catalyst to increase its selectivity to ethylene when used in the production of light olefins from oxygenated compounds which comprises contacting, and incorporating with said catalyst a phosphonitrilic oligomer formed of phosphazo groups having the formula

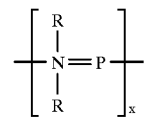

wherein the substituent R is the same or different, and is selected from a group consisting of halogen, alkenyl, alkynyl, alkyl, cycloalkyl, aryl, aralkyl, alkaryl, and alkoxy χ ranges from about 3 to about 100, the oligomer formed from the phosphazo groups is either linear or cyclic, and calcining said catalyst with which the phosphonitrilic oligomer has been incorporated at temperature sufficient to decompose said phosphonitrilic oligomer, and deposit on the catalyst from about 0.001 percent to about 50 percent phosphorus, based on the total weight of the phosphorus-containing catalyst.

2. The process of claim 1 wherein the phosphonitrilic oligomer comprises a phosphonitrilic halide trimer.

3. The process of claim 2 wherein the phosphonitrilic halide trimer is a phosphonitrilic chloride trimer.

4. The process of claim 1 wherein from about 0.05 percent to about 40 percent phosphorus is deposited on the catalyst.

5. The process of claim 1 wherein the phosphonitrilic oligomer is dispersed, or dissolved in a solvent, impregnated into the catalyst, dried, and then calcined to increase the ethylene selectivity of the catalyst.

6. The process of claim 1 wherein the small pore molecular sieve catalyst is of pore size ranging from about 5.0 Å to about 4.0 Å.

7. The process of claim 6 wherein the small pore molecular sieve catalyst is of pore size ranging from about 4.8 Å to about 4.4 Å.

8. The process of claim 6 wherein the small pore molecular sieve catalyst is selected from the group consisting of zeolites, tetrahedral aluminophosphates, and tetrahedral silicoalumino-phosphates.

9. The process of claim 6 wherein the small pore molecular sieve catalyst is selected from the group consisting of ZSM-34, ZK-4, ZK-5, zeolite A, zeolite T, chabazite, gmelinite, clinoptilolite, erionite, ZSM-35, rho, offretite, ferrierite, levyne, SAPO-17, SAPO-18, SAPO-34, SAPO-43 and SAPO44.

* * * * *